US00PP09681P

United States Patent [19]

Olsen et al.

[11] Patent Number: Plant 9,681

[45] Date of Patent: Nov. 5, 1996

[54] APPLE TREE 'OLSENTWO GALA'

[76] Inventors: Richard R. Olsen; Larry M. Olsen, both of Rte. 2, Box 2400, Prosser, Wash. 99350

[21] Appl. No.: 377,288

[22] Filed: Jan. 23, 1995

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

| | | | |
|---|---|---|---|
| P.P 3,637 | 10/1974 | McKenzie | Plt./34.1 |
| P.P. 4,121 | 10/1977 | Ten Hove | Plt./34.1 |
| P.P. 6,172 | 5/1988 | Creech | Plt./34.1 |
| P.P. 6,955 | 8/1989 | Kiddle | Plt./34.1 |
| P.P. 7,396 | 12/1990 | Cooper | Plt./34.1 |
| P.P. 7,589 | 7/1991 | Fulford et al. | Plt./34.1 |
| P.P 8,621 | 3/1994 | Olsen et al. | Plt./34.1 |
| P.P. 8,673 | 4/1994 | Waliser | Plt./34.1 |
| P.P 8,702 | 5/1994 | Hill | Plt./34.1 |

*Primary Examiner*—James R. Feyrer
*Attorney, Agent, or Firm*—Chernoff, Vilhauer, et al.

[57] ABSTRACT

This new and distinct Gala apple cultivar is the result of a whole tree mutation of the Tenroy cultivar (U.S. Plant Pat. No. 4,121). The fruit of this cultivar is distinguished by its attractive bright Nopal Red undercolor overlain by darker Nopal Red stripes covering 90–100% of the fruit surface, the timing of color development, and by its improved storage life.

6 Drawing Sheets

BACKGROUND AND SUMMARY OF THE INVENTION

This invention relates to a new and distinct strain of the Gala apple variety. Applicant's assignee intends to sell trees of the subject variety under the trademark Pacific Gala. This new cultivar originated as a whole tree mutation of Royal Gala (Tenroy cultivar U.S. Plant Pat. No. 4,121) and was discovered by Richard Ralph Olsen and Larry Martin Olsen August 1989 in a four year old solid 10-acre bloc of Tenroy cultivar located at Olsen Bros. Ranches, Inc. ranch #11, Prosser, Wash. 99350, USA The fruit coloration was noted as having a distinctly different color than the Tenroy cultivar, Regal Gala (Fulford Cultivar U.S. Plant Pat. No. 7,589) and the Galaxy Gala (Kiddle cultivar U.S. Plant Pat. 6,955), and having a much more intense stripe overlay than the nearby UltraRed Gala (Obrogala cultivar U.S. Plant Pat. No. 8,621 and also originating on this ranch), the Waliser cultivar U.S. Plant Pat. No. 8,673 and the Fulford cultivar (which has no striping characteristic).

Asexual reproduction of the new cultivar was done by budding and grafting and the resulting second generation trees show that the foregoing characteristics and distinctions come true and are established and transmitted through suceeding propagations. Fruit from this new cultivar, hereafter referred to as the Olsentwo cultivar, that is described and compared, came from two different site locations. This was necessary to reliably compare our new invention with those known other redder strains of the Gala apple Variety. At Olsen Bros. Ranch #11, Olsentwo cultivar of the original tree was compared to both the Tenroy cultivar (adjacent trees) and the nearby Obrogala cultivar (original tree). Kiddle cultivar had been budded in to an Olsenteo cultivar tree for comparison and fruit from this selection indicated a distinct color difference, but fruit sample numbers were not sufficient to run a valid comparison. Olsentwo cultivar was directly compared to the Kiddle and Fulford cultivar at a second location—Ridgeview Orchards, Prosser, Wash.—some 15 miles distant of Olsen Bros. Ranch #11. The only difference noted of the Olsentwo cultivar between the two production sites was the color chroma/hue and related calorimetric readings. All other characteristics of the cultivar were the same between the site locations (Table 1).

Fruit of the Waliser cultivar was acquired for comparison from the John Dobbler Orchard, Matawa, Wash., some 70 miles distant from Olsen Bros.' Ranch #11.

Compared fruit from Tables 1 to 2 were from trees propagated on M7 rootstock of similar age and having central leader training with similar pruning pratices.

Extensive search for bearing and/or planted acreage of the Applewaites cultivar U.S. Plant Pat. No. 8,720 was unsuccessful and it is our belief that there is no bearing or planted source of the Applewaites cultivar in the United States. Patent description of the Applewaites cultivar indicates that it is similar to the blush characteristic of Fulford cultivar, but differs from the Fulford cultivar in the percent fruit surface colored and the maturity timing.

No similarities were observed between Olsentwo cultivar and the Cooper U.S. Plant Pat. No. 7,396 and Creech U.S. Plant Pat. No. 6,172 cultivars. Other than maturity timing, the Cooper and Creech cultivars were not compared in detail.

The following characteristics are particularly outsanding in our new variety:

(1) The color of the fruit, both the undercolor and stripe overcolor, in conjunction, result in Olsentwo cultivar having a distinctly different appearance than the other striped cultivars to which it is compared. When the red coloration of the subject variety is different in hue than the compared varieties, i.e., Tenroy and Kiddle cultivars, then the stripes of Olsentwo cultivar are not as intense as those of the compared cultivars. When the red coloration of the subject variety is similar in hue to the similar varieties, i.e., the Obrogala cultivar, then the striping pattern is generally more intense and prominent in the subject variety, (2) The completness and uniformity of the color development seen with Olsentwo cultivar is similar to that seen with the Obrogala and Waliser cultivars—where all the fruit have 90 to 100% of the surface area covered, and considerably better than that noted with the Kiddle cultivar—where the surface area colored falls in the 70 to 100% range with 50% of the fruit falling in the under 90% color range.

(3) Undercolor development of Olsentwo is similar in timing to that of the Obrogala and Waliser cultivars and is similar in timing to that of Obrogala cultivar, and is five days ahead of Kiddle cultivar and 10 days ahead of Tenroy cultivar. The stripe overcolor initiation is similar in timing for all striped cultivars compared. Like the Tenroy and Kiddle cultivars, the striped remain very distinct at harvest maturity in the subject variety.

(4) Seed colors from equally mature fruit shows that Olsentwo cultivar seed is distinct in color from that seen with Tenroy, Kiddle, Fulford and Obrogala cultivar; that the color is uniform over the entire seed surface like the Tenroy and Kiddle cultivars and not bi-colors as that seen with Obrogala.

(5) Three-year-old wood samples show that Olsentwo cultivar exhibits a slighty lighter color bloc than that seen with the Tenroy cultivar, a darker color bloc than that observed with the Kiddle cultivar, and an appreciably darker color bloc than that exhibited by the Obrogala cultivar. The hues of the individual cultivar colors are very similar with the exception of the Obrogala cultivar which is appreciably lighter.

(6) Storage of harvested fruit exhibiting similar internal ripeness conditions in both common and Controlled Atmosphere conditions show that Olsentwo cultivar, along with Obrogala cultivar, has greater storage life than that of Kiddle cultivar and Tenroy cultivar as exhibited by shriveling and interal maturity indices. Obrogala cultivar exhibits slightly better internal fruit conditions than Olsentwo cultivar after three months common storage.

(7) The Olsentwo cultivar has a striped overlay as do the Tenroy, Obrogala, Kiddle and Waliser cultivars, whereas the Fulford and Applewaites cultivar do not. The intensity of the striping can be positioned between the grouping of Tenroy and Kiddle cultivars and the grouping of Obrogala and Waliser cultivars.

(8) Order of ripening of the newer red sport gala cultivars, as indicted by internal starch indices of the compared fruit: (Waliser cultivar=+4 , Tenroy cultivar=0 (standard), Obrogala cultivar=0, Cooper cultivar=0, Kiddle cultivar=0, Creech cultivar=0, Olsentwo cultivar=−2, Fulford cultivar=−7, Applewaites cultivar=−9), places Olsentwo cultivar ahead of Waliser, Obrogala and Kiddle cultivars, but behind the Fulford and Applewaites cultivars.[1]

The above mentioned characteristic differences of our new cultivar of the Gala apple variety is summarized in greater detail in the following table. Color related data is an average of a 40-fruit sample of each cultivar, and the internal maturity indices is an average of a 10-fruit sample of each cultivar.

TABLE 1

| | Ridgeview Orchard | | |
|---|---|---|---|
| | Kiddle cv. | Olsentwo cv. | Fulford cv. |
| Fruit Color | | | |
| Undercolor[2] | 37–7 | 39–14 | 28–3 |
| Overstripe[2] | 37–13 | 38–11 | |
| Overcolor[2] | — | — | 40–12 |
| % coverage | 70–100 | –90–100 | — |
| % fruit with 90+ % coverage | 50 | 100 | 40 |
| L, a, b calorimetric readings[3] | | | |
| L | 36.04 | 31.89 | 55.78 |
| a | 31.92 | 32.94 | 28.63 |
| b | 11.79 | 9.91 | 23.05 |
| Undercolor Development | –5 days | –10 days | –15 days |
| Stripe[4] | 5 | 3 | 0 |
| Seed Color[2] | 34–15 | 32–15 | 28–13 |
| Wood Color[2] | 32–15 | 34–16 | — |
| Condition After Storage % fruit shriveled | | | |
| 3-mo common | 100 | 0 | 100 |

TABLE 1-continued

| | Olson Bros. Ranch 11 | | | | | | | | |
|---|---|---|---|---|---|---|---|---|---|
| | Olsentwo cv. | | | Obrogala cv. | | | Tenroy cv. | | |
| Fruit Color | | | | | | | | | |
| Undercolor[2] | 40–14 | | | 40–14 | | | 37–7 | | |
| Overstripe[2] | 39–11 | | | 39–12 | | | 37–1 | | |
| % coverage | 90–100 | | | 90–100 | | | 50–90 | | |
| % fruit with 90+ % coverage | 100 | | | 100 | | | 20 | | |
| L, a, b calorimetric readings[3] | | | | | | | | | |
| L | 34.15 | | | 35.28 | | | 47.76 | | |
| a | 30.70 | | | 32.21 | | | 27.54 | | |
| b | 9.73 | | | 11.55 | | | 16.49 | | |
| Undercolor development | –10 days | | | –10 days | | | 0 standard | | |
| Stripe[4] | 3 | | | 1 | | | 7 | | |
| Seed Color[2] | 32–15 | | | 30–11/30–16 | | | 34–15 | | |
| Wood Color[2] | 34–16 | | | 29–14 | | | 35–15 | | |
| Condition After Storage % fruit shriveled | | | | | | | | | |
| 3-mo common | 100 | | | 0 | | | — | | |
| 3-mo CA | — | | | — | | | — | | |
| Internal indices[1] | Pr. | °B | St. | Pr. | °B | St. | Pr. | °B | St. |
| 3-mo CA | | | | | | | | | |
| In | 18.8 | 9.8 | 2.3 | 20.1 | 11.3 | 2.7 | 18.8 | 9.9 | 2.8 |
| Out | 16.2 | 15.0 | 5.4 | 17.7 | 16.0 | 5.3 | 15.6 | 13.1 | 5.5 |

TABLE 2

| | Olsen Bros. Ranch 11 | |
|---|---|---|
| | Olsentwo cv. | Tenroy cv. |
| Fruit Color | | |
| Undercolor[2] | 40–14 | 37–7 |
| Overstripe[2] | 37–11 | 37–1 |
| % coverage | 90–100 | 50–90 |
| % fruit with 90+ % coverage | 100 | 20 |
| Undercolor development | –10 days | 0 standard |
| Stripe[4] | 3 | 7 |
| Seed Color[2] | 32–15 | 34–15 |

TABLE 2-continued

| Internal indices[1] | Condition At Harvest Pr. | °B | St. | Pr. | °B | St. |
|---|---|---|---|---|---|---|
| | 18.5 | 10.5 | 2.3 | 19.0 | 10.0 | 1.8 |

| | Dobbler Orchard | |
|---|---|---|
| | Waliser cv. | Tenroy cv. |
| Fruit Color | | |
| Undercolor[2] | 40–13 | 37–6 |
| Overstripe[2] | 40–14 | 37–3 |
| % coverage | 90–100 | 60–90 |
| % fruit with 90+ % coverage | 95 | 30 |
| Undercolor development | −10 days | 0 standard |
| Stripe[4] | 7 | 7 |
| Seed Color[2] | 28–13 | 34–16 |

| Internal indices[1] | Condition At Harvest Pr. | °B | St. | Pr. | °B | St. |
|---|---|---|---|---|---|---|
| | 21.3 | 11.4 | 3.2 | 18.4 | 12.6 | 3.4 |

[1]Internal indices as measured represent flesh resistance to pressure (Pr.), refractometer reading in °Brix (°B), and a starch/iodine reading using the independent Washington State Apple Maturity Program scale of 1 to 6 where one is full starch and 6 is free of starch (St.)
[2]Color numbers from the Munsell Limited Color Cascade.
[3]The calorimetric readings are an average of the measurements of the L, a, b color solids in a three-dimensional color chart created by Hunter Lab, Reston, Virginia. This instrument is used to help in quantifying the Washington State Apple Commission color grade standards. The calorimeter reads on three scales and each scale corresponds to an axis of a three-dimensional color model:
L axis represents white to black with 0 = black and 100 = white
a axis = +numbers are red with the higher number being redder
b axis = +numbers are the yellows with the higher number being the yellowest; negative numbers represent the blues.
[4]A subjective rating scale of 0–7 where 0 equals no stripes seen and 7 equals that striping associated with the standard Tenroy cultivar, i.e., very distinct and abundant stripes.

DETAILED DESCRIPTION OF THE DISCLOSURE

Figure 1:
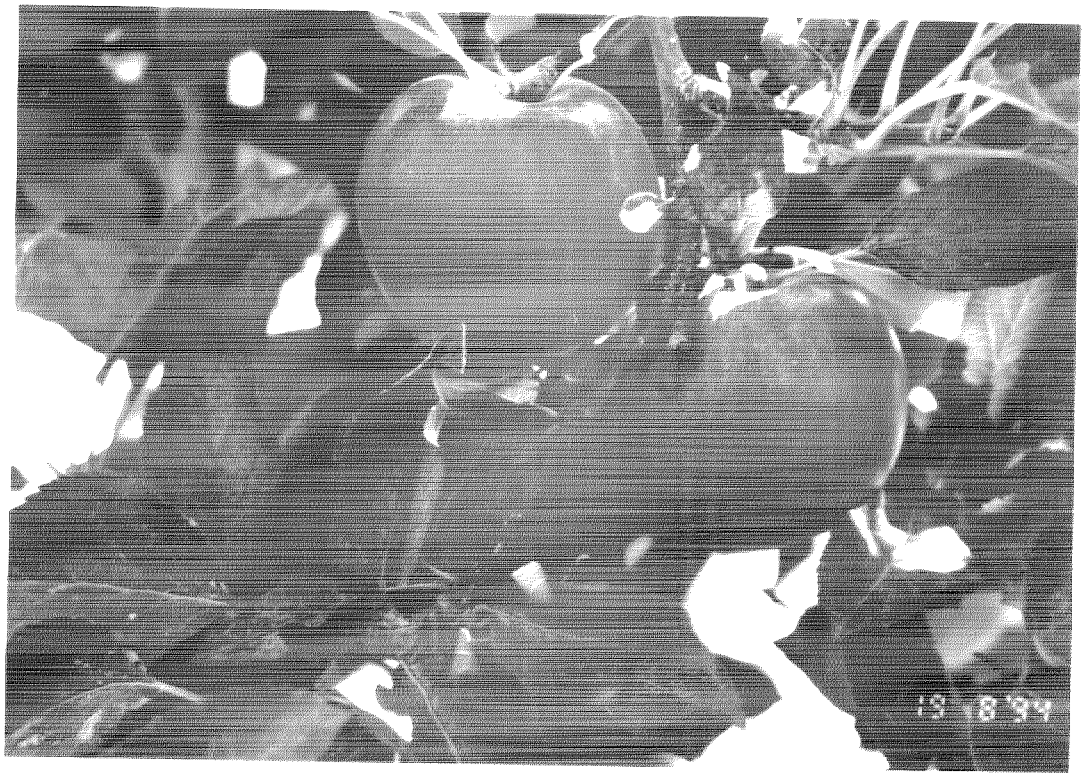
FIG. 1 is a view of second generations fruit illustrating the full and intense coloration pattern of our new cultivar of the Gala variety.
Figure 2:
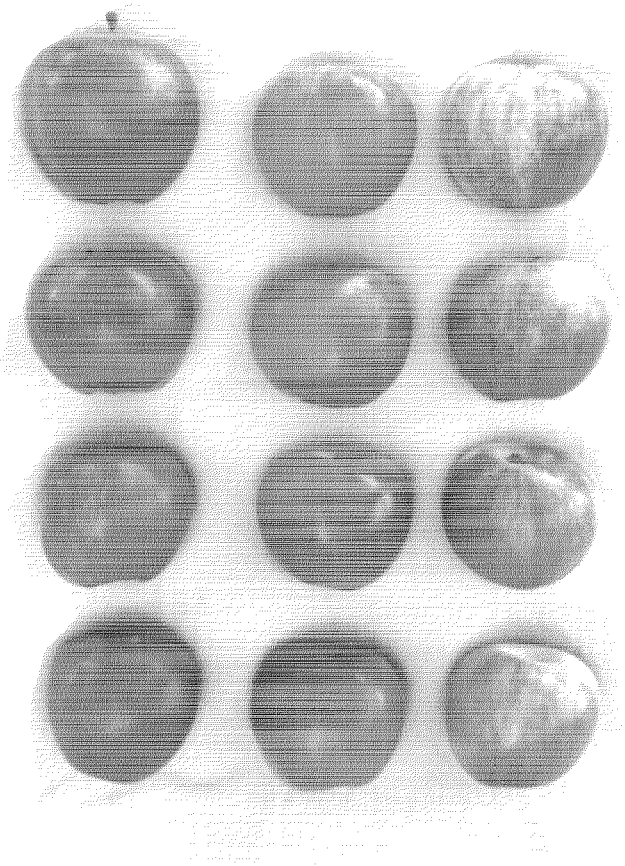
FIG. 2 is composite view of three cultivars from the Ridgeview Orchard site illustrating color and pattern differences between (left to light) Kiddle cultivar, Olsentwo cultivar, and Tenroy cultivar, respectively.
Figure 3:
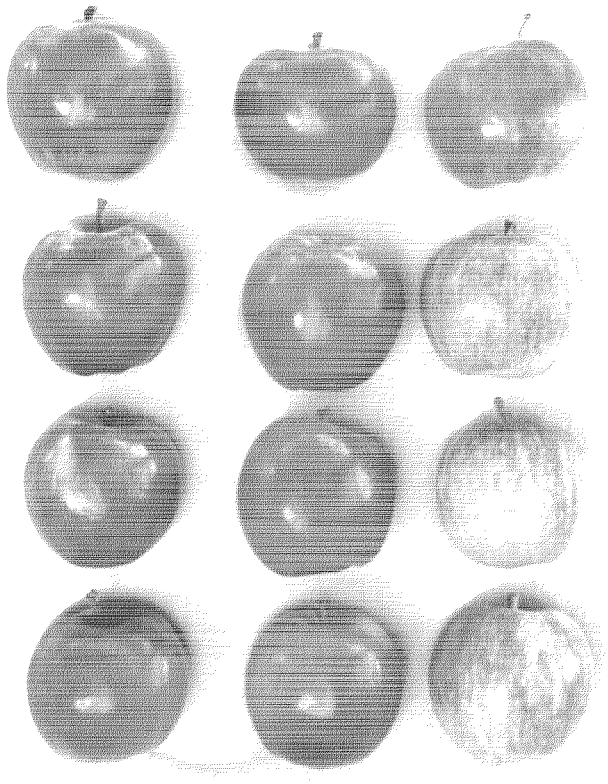
FIG. 3 is a composite view of three cultivars from the Olsen Bros. Ranch #11, taken at the same time as FIG. 2, illustrating color and pattern differences between (left to right) Obrogala cultivar, Olsentwo cultivar, and Tenroy cultivar respectively.
Figure 4:
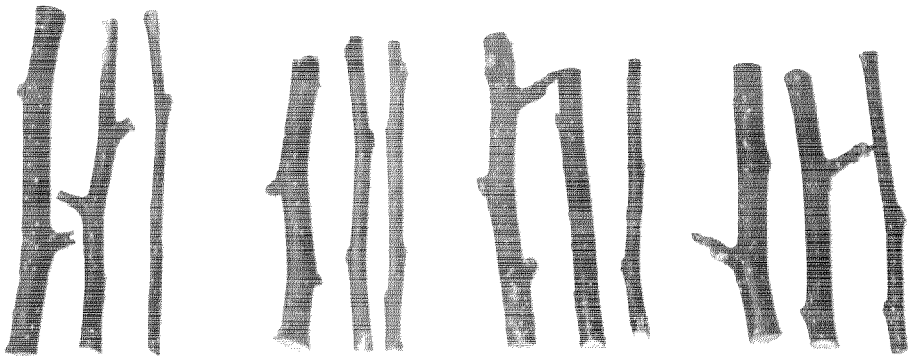
FIG. 4 is a composite view of four cultivars illustrating, from right to left, sections of one, two and three-year-old branches and their differences in bark coloration. Cultivars from left to right are Olsentwo, Obrogala, Kiddle, and Tenroy.
Figure 5:
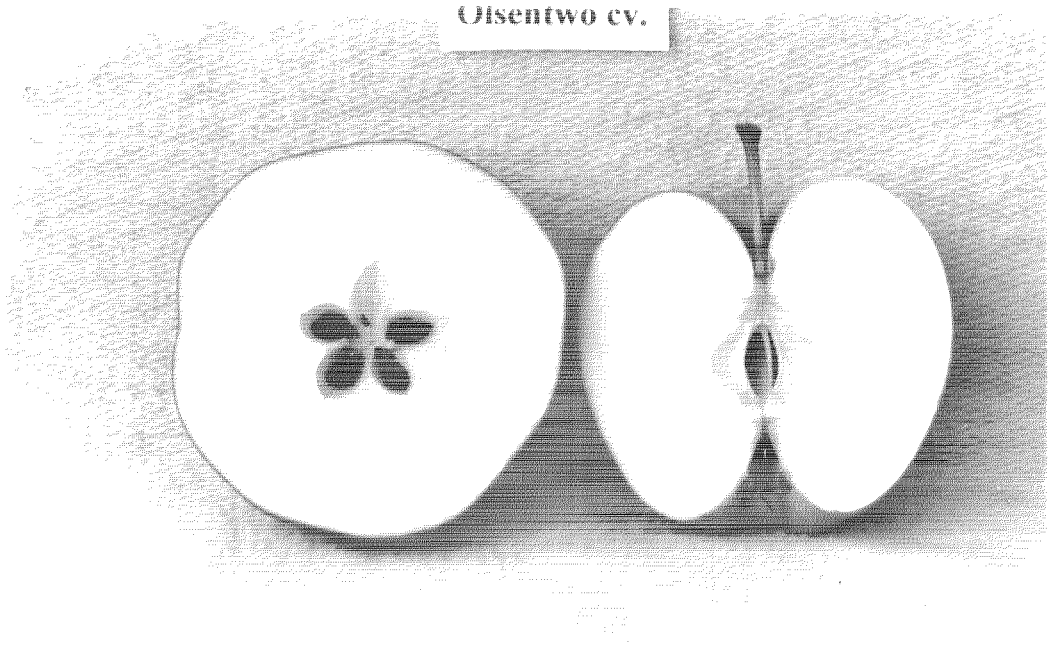
FIG. 5 is composite view of the median horizontal and tangential sections of fruit from our new Gala cultivar and illustrating the core area as herein described.
Figure 6:
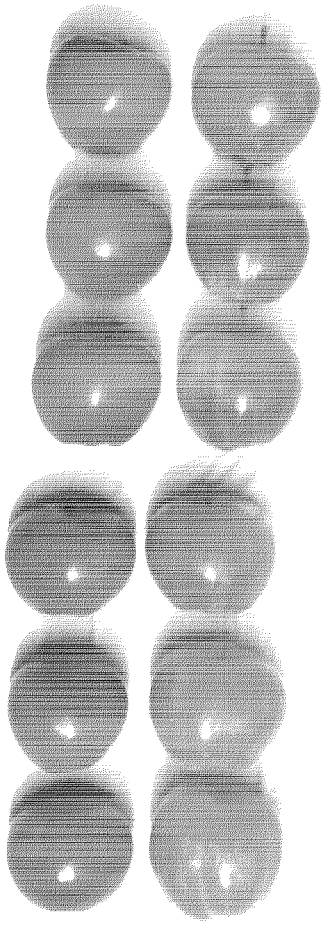
FIG. 6 is a composite view of fruit of (left to right) Waliser and Tenroy cultivars from the John Dobbler Orchard illustrating color and pattern differences.

Tree: Medium; vigorous, upright-spreading; round-topped, hardy, productive; regular bearing.

Trunk: Medium stocky, medium smooth.

Branches: Medium thickness, smooth; much branching; color of three-year-old wood #34–16 of *Munsell Limited Color Cascade.*

*Lenticels.*—Numerous, medium size; color #28–4 of *Munsell Limited Color Cascade.*

Leaves:

*Length.*—3½ to 4¼".

*Width.*—1¾ to 2½"; medium large; medium wide; medium long; oval, abruptly pointed.

*Margin.*—Crenate; finely serrate.

Flowers: Medium bloom time, first bloom Apr. 12, 1994 , full bloom Apr. 15, 1994 (Prosser, Wash.), medium size; color is white with pink fading to white on reverse side.

Fruit:

*Original tree.*—First picking Aug. 22, 1994, second (final) picking Aug. 29, 1994. As described eating ripe.

*Form.*—Uniforms; round-conical, slightly irregular.

*Size.*—Axial diameter 3–3¼"; transverse 2 ⅝ to 3⅛".

*Cavity.*—Symmetrical, abrupt at base; apex acuminate; depth ¾"; breadth 1¼", wanting russet markings.

*Basin.*—Symmetrical, rounded, undulate; markings none; depth 3/18"; breadth ¾ to 1 ".

*Stem.*—Medium stout, pubescent, length 1"; breadth ⅛".

Calyx: Generally closed.

*Segments.13* Persistent; approximate; lanceolate; erect, lightly reflexed from base at apex; length ¼".

*Outer surface.*—Pubescent.

*Inner surface.*—Pubescent.

Eye: Medium in Size.

Skin: Thin; smooth glossy, waxed, dots conspicuous, many, small, circular, evenly distributed.

*Color of dots.*—Pale whitish yellow.

*Ground color.*—#26–2 of the *Munsell Limited Color Cascade* ; limited to 10% or less of the surface area.

*Color markings.*—Striped overcolor #40–14 with an undercolor #39–11 of *Munsell Limited Color Cascade*; bright. Hunter Lab calorimetric readings: L =32.15, a=30.70, b =9.73 .

*Bloom.*—Moderate.

*Scarfskin.*—None to Wanting; white; basal area only.

General color effect:

*Flesh.*—Juicy, satiny, creamy white. Texture: Firm; tender, fine; crisp. Flavor: Mild, delicate rich; aromatic. Quality: Best.

*Core.*—Medium position. Bundle area: Small. oblate. Bundles: Inconspicuous; in one whorl. Core lines: Clasping; indistinct. Calyx-tube: Funnel form; glabrous towards base. Stem of funnel: Long. Depth of tube to shoulder: 3/16". Entire depth: 7/16". Stiles: Present. Stamens: One distinct whorl, medium position. Auxiliary cavity: Present. Seed cells: Open. Cell walls: Thin; tough. Length: ⅝". Breadth: ⅜". Longitudinal section: Ovate; obtuse at apex. Surface: Smooth. Cross section: Broad.

*Seeds.*—Perfect, #10. Number in one cell: 2. Length: 5/16". Breadth: 3/16". Color: #32–15 of the *Munsell Limited Color Cascade.*

Use: Market, dessert.

Keeping quality: Good—three to four months CA Storage.

Resistance to:

*Insects.*—Good.

*Diseases.*—Good.

What is claimed is:

1. A new and distinct variety of Gala apple tree as herein shown and described and characterized particularly by the intense bright color of its fruit, the distinct red-on-red striped color pattern of its fruit, the high percentae of coloration of its fruit, including those in the interior of the tree, and its quality following storage.

* * * * *

UNITED STATES PATENT AND TRADEMARK OFFICE

CERTIFICATE OF CORRECTION

PATENT NO. : Plant 9,681

DATED : November 5, 1996

INVENTOR(S) : Richard R. Olsen; Larry M. Olsen

It is certified that error appears in the above-identified patent and that said Letters Patent is hereby corrected as shown below:

Column 1, line 12, insert --.-- after USA;

Column 4, line 58, table 2, column 2, delete "37-11" and insert --39-11--;

Column 6, line 32, after "Segments." delete "13";

Column 6, line 45, delete "L=32.15" and insert --L=34.15--;

Column 6, line 52, delete "Small. oblate." and insert --Small, oblate.--

Signed and Sealed this

Twenty-fifth Day of March, 1997

*Attest:*

*Attesting Officer*

Bruce Lehman

BRUCE LEHMAN

*Commissioner of Patents and Trademarks*